(12) United States Patent
Slamon et al.

(10) Patent No.: US 7,537,905 B2
(45) Date of Patent: May 26, 2009

(54) AMPLIFIED AND OVEREXPRESSED GENE IN COLORECTAL CANCERS

(75) Inventors: Dennis J. Slamon, Woodland Hills, CA (US); Lee A. Anderson, Los Angeles, CA (US); Charles L. Ginther, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 482 days.

(21) Appl. No.: 10/346,367

(22) Filed: Jan. 15, 2003

(65) Prior Publication Data

US 2004/0137442 A1 Jul. 15, 2004

(51) Int. Cl.
*G01N 33/574* (2006.01)
(52) U.S. Cl. .......................................... 435/7.23; 435/6
(58) Field of Classification Search ........................ None
See application file for complete search history.

(56) References Cited

U.S. PATENT DOCUMENTS

| | | | |
|---|---|---|---|
| 6,326,148 B1 | 12/2001 | Pauletti et al. | |
| 2002/0182586 A1* | 12/2002 | Morris et al. | 435/4 |

FOREIGN PATENT DOCUMENTS

WO    WO 98/02539    1/1998

OTHER PUBLICATIONS

Sambrook et al, Molecular Cloning, A Laboratory Manual, Cold Spring Harbor Press, 1989.*
Li et al, Clin Cancer Res 11:1809-1814, 2005.*
Zhang et al., "Cloning and Functional Analysis of cDNAs with Open Reading Frames for 300 Previously Undefined Genes Expressed in CD34+ Hematopoietic Stem/Progenitor Cells", *Genome Research* 10:1546-1560 (2000).
Kalliioniemi, "Detection and mapping of amplified DNA sequences in breast cancer by comparative genomic hybridization" *Proc. Natl. Acad. Sci. USA* 91:2156-2160 (1994).
Schlegal et al., "Comparative Genomic in Situ Hybridization of Colon Carcinomas with Replication Error" *Cancer Research* 55:6002-6005 (1995).
Ried, et al., "Comparative Genomic Hybridization Reveals s Specific Pattern of Chromosomal Gains and Losses During the Genesis of Colorectal Tumors" *Genes, Chromosomes & Cancer* 15:234-245 (1996).
Nakao et al., "Genetic Changes in Primary Colorectal Cancer by Comparative Genomic Hybridization" *Jpn. J. Surg.* 28:567-569 (1998).
Sambrook et al., "Extraction, Purification, and Analysis of Messenger RNA from Eukaryotic Cell," in *Molecular Cloning, A Laboratory Manual*, 2nd Edition: p. 7.39, Cold Springs Harbor Laboratory Press (1989).

* cited by examiner

*Primary Examiner*—Misook Yu
*Assistant Examiner*—Mark Halvorson
(74) *Attorney, Agent, or Firm*—Townsend and Townsend and Crew LLP

(57) ABSTRACT

This invention relates to methods to diagnose colon cancer and other proliferative diseases. Gene 26#77 is identified herein as a novel oncogene. Methods are provided for diagnosing and treating a disease or disorder characterized by amplification of the 26#77 gene and/or overexpression of 26#77 gene products. The 26#77 gene is located on chromosome 20q13.2, a region whose amplification is associated with a poor cancer prognosis. The 26#77 gene is amplified and 26#77 RNA and protein are overexpressed in 60% of colorectal cancers.

15 Claims, 1 Drawing Sheet

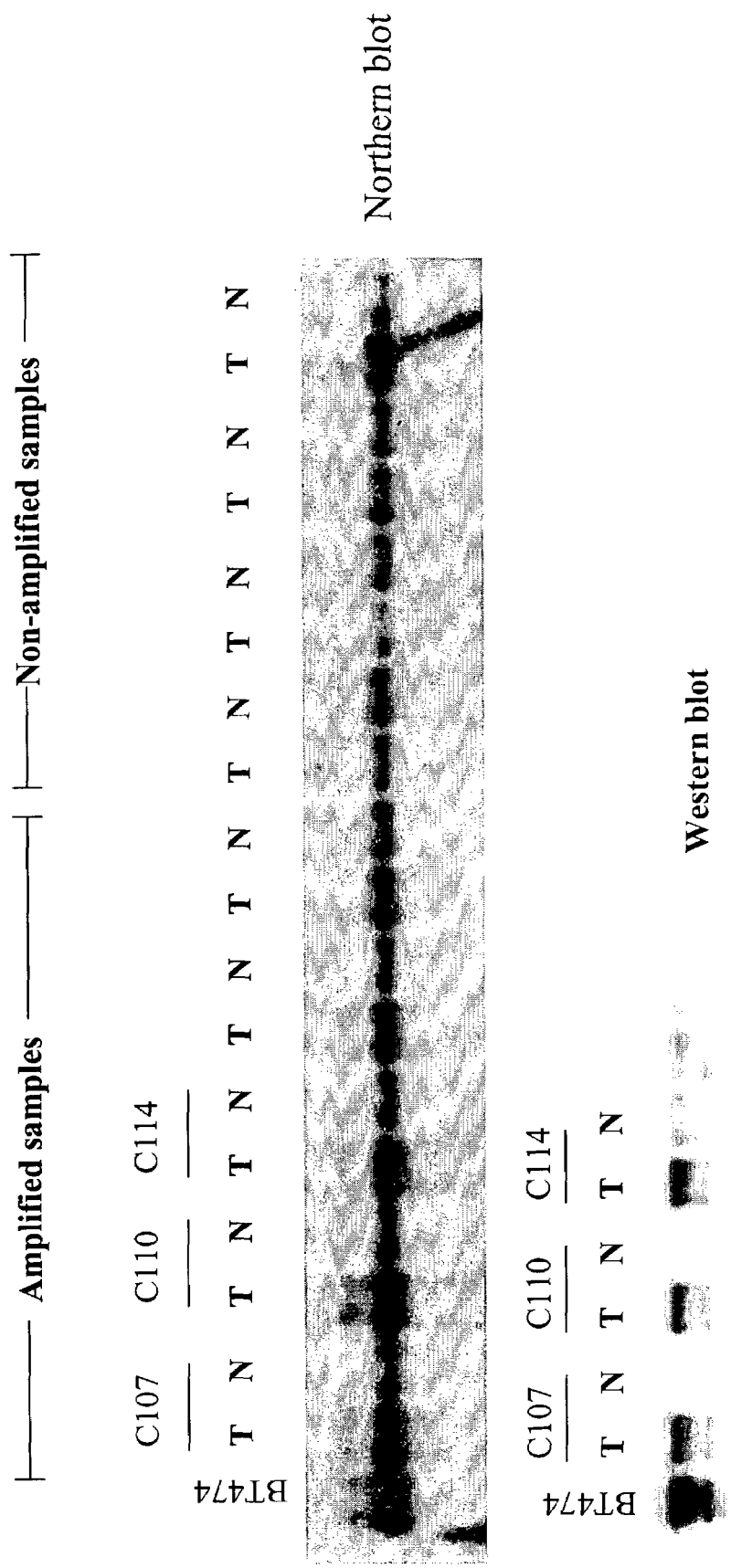

SEQUENCE LISTING

<160> NUMBER OF SEQ ID NOS: 2

<210> SEQ ID NO 1
<211> LENGTH: 1605
<212> TYPE: DNA
<213> ORGANISM: Homo sapiens
<220> FEATURE:
<223> OTHER INFORMATION: 26#77 protein

<400> SEQUENCE: 1

```
ctttgggggt tgctgctgg ctctgactcc cgtcctgcga tgggttgcga cggggggaaca      60 atccccaaga ggcatgaact ggtgaagggg ccgaagaagg ttgagaaggt cgacaaagat     120
gctgaattag tggcccaatg gaactattgt actctaagtc aggaaatatt aagacgacca     180
atagttgcct gtgaacttgg cagactttat aacaaagatg ccgtcattga atttctcttg     240
gacaaatctg cagaaaaggc tcttgggaag gcagcatctc acattaaaag cattaagaat     300
gtgacagagc tgaagctttc tgataatcct gcctgggaag gggataaagg aaacactaaa     360
ggtgacaagc acgatgacct ccagcgggcg cgtttcatct gccccgttgt gggcctggag     420
atgaacggcc gacacaggtt ctgcttcctt cggtgctgcg gctgtgtgtt ttctgagcga     480
gccttgaaag agataaaagc ggaagtttgc cacacgtgtg gggctgcctt ccaggaggat     540
gatgtcatcg tgctcaatgg caccaaggag gatgtggacg tgctgaagac aaggatggag     600
gagagaaggc tgagagcgaa gctggaaaag aaaacaaaga aacccaaggc agcagagtct     660
gtttcaaaac cagatgtcag tgaagaagcc ccagggccat caaaagttaa gacagggaag     720
cctgaagagg ccagccttga ttctagagag aagaaaacca acttggctcc caaaagcaca     780
gcaatgaatg agagctcttc tggaaaagct gggaagcctc cgtgtggagc cacaaagagg     840
tccatcgctg acagtgaaga atcggaggcc tacaagtccc tctttaccac tcacagctcc     900
gccaagcgct ccaaggagga gtctgcccac tgggtcaccc acacgtccta ctgcttctga     960
agcccgcact gccaccgctc ctgccccaga aggttgttta gtttccacgt aggcaggtcg    1020
ctttgtgcct ctgagtgcgc tgctgtgtgt tctctctata gttctgcgtc ataaagctgt    1080
cctggccagc cttcaagctg gtgtggccac tcttgatgtg aggcgtgtcg gttccagggg    1140
ggacatggga ggggctgcac agtggcccga ggtcatgctt gcttccacct gcaggtgcat    1200
ttggtccttt ccatggccag gaagcccgtg gggctgcact ttttatgctt gcagtagcaa    1260
gagactccag agtcctcacc ggtgcagagt tggcacatat taattaacta aaattctaat    1320
gatcttgcta ccagcaataa atcaagtagg ccaagtgaaa ctgggcttta aaaaggatgg    1380
atttcaaata cactgtgccc actagaagct tcgaagggcc tcgtccctct gctacagccc    1440
```

```
tgggaggagc caggatcctt gttggtctag ctaaatactg ttaggggagt gtgccccatc    1500
tcatcatttc gaagatagca gagtcatagt tgggcacccg gtgattgggt tcaaaaataa    1560
agctggtctg cctcttctca aaaaaaaaaa aagaaaaaa aaaaa                     1605
```

<210> SEQ ID NO 2
<211> LENGTH: 306
<212> TYPE: PRT
<213> ORGANISM: Homo sapiens
<220> FEATURE:
<223> OTHER INFORMATION: 26#77 protein

<400> SEQUENCE: 2

```
Met Gly Cys Asp Gly Gly Thr Ile Pro Lys Arg His Glu Leu Val Lys
  1               5                  10                  15

Gly Pro Lys Lys Val Glu Lys Val Asp Lys Asp Ala Glu Leu Val Ala
             20                  25                  30

Gln Trp Asn Tyr Cys Thr Leu Ser Gln Glu Ile Leu Arg Arg Pro Ile
         35                  40                  45

Val Ala Cys Glu Leu Gly Arg Leu Tyr Asn Lys Asp Ala Val Ile Glu
     50                  55                  60

Phe Leu Leu Asp Lys Ser Ala Glu Lys Ala Leu Gly Lys Ala Ala Ser
 65                  70                  75                  80

His Ile Lys Ser Ile Lys Asn Val Thr Glu Leu Lys Leu Ser Asp Asn
                 85                  90                  95

Pro Ala Trp Glu Gly Asp Lys Gly Asn Thr Lys Gly Asp Lys His Asp
            100                 105                 110

Asp Leu Gln Arg Ala Arg Phe Ile Cys Pro Val Val Gly Leu Glu Met
        115                 120                 125

Asn Gly Arg His Arg Phe Cys Phe Leu Arg Cys Cys Gly Cys Val Phe
    130                 135                 140

Ser Glu Arg Ala Leu Lys Glu Ile Lys Ala Glu Val Cys His Thr Cys
145                 150                 155                 160

Gly Ala Ala Phe Gln Glu Asp Asp Val Ile Val Leu Asn Gly Thr Lys
                165                 170                 175

Glu Asp Val Asp Val Leu Lys Thr Arg Met Glu Glu Arg Arg Leu Arg
            180                 185                 190

Ala Lys Leu Glu Lys Lys Thr Lys Pro Lys Ala Ala Glu Ser Val
        195                 200                 205

Ser Lys Pro Asp Val Ser Glu Glu Ala Pro Gly Pro Ser Lys Val Lys
    210                 215                 220

Thr Gly Lys Pro Glu Glu Ala Ser Leu Asp Ser Arg Glu Lys Lys Thr
225                 230                 235                 240

Asn Leu Ala Pro Lys Ser Thr Ala Met Asn Glu Ser Ser Gly Lys
                245                 250                 255

Ala Gly Lys Pro Pro Cys Gly Ala Thr Lys Arg Ser Ile Ala Asp Ser
            260                 265                 270

Glu Glu Ser Glu Ala Tyr Lys Ser Leu Phe Thr Thr His Ser Ser Ala
        275                 280                 285

Lys Arg Ser Lys Glu Glu Ser Ala His Trp Val Thr His Thr Ser Tyr
    290                 295                 300

Cys Phe
305
```

AMPLIFIED AND OVEREXPRESSED GENE IN COLORECTAL CANCERS

STATEMENT AS TO RIGHTS TO INVENTIONS MADE UNDER FEDERALLY SPONSORED RESEARCH AND DEVELOPMENT

This invention was made with Government support by Grant No. CA32737, awarded by the National Institutes of Health. The Government has certain rights in this invention.

FIELD OF THE INVENTION

This invention relates to methods to diagnose colon cancer and other proliferative diseases.

BACKGROUND OF THE INVENTION

Chromosome abnormalities are often associated with genetic disorders, degenerative diseases, and cancer. The deletion or multiplication of copies of whole chromosomes and the deletion or amplifications of chromosomal segments or specific regions are common occurrences in cancer (Smith (1991) *Breast Cancer Res. Treat.* 18: Suppl. 1:5-14; van de Vijer (1991) *Biochim. Biophys. Acta.* 1072:33-50). In fact, amplifications and deletions of DNA sequences can be the cause of a cancer. For example, proto-oncogenes and tumor-suppressor genes, respectively, are frequently characteristic of tumorigenesis (Dutrillaux (1990) *Cancer Genet. Cytogenet.* 49: 203-217). Clearly, the identification and cloning of specific genomic regions associated with cancer is crucial both to the study of tumorigenesis and in developing better means of diagnosis and prognosis.

One of the amplified regions found in studies of breast and colon cancer cells is on chromosome 20, specifically, 20q13.2 (see, e.g. WO98/02539). Amplification of 20q13.2 was subsequently found to occur in a variety of tumor types and to be associated with aggressive tumor behavior. Increased 20q13.2 copy number has been found in 40% of breast cancer cell lines and 18% of primary breast tumors (Kalliioniemi (1994) *Proc. Natl. Acad. Sci. USA* 91: 2156-2160). Copy number gains at 20q13.2 have also been reported in greater than 25% of cancers of the ovary (Iwabuchi (1995) *Cancer Res.* 55:6172-6180), colon (Schlegel (1995) *Cancer Res.* 55: 6002-6005 and WO02/06526), head-and-neck (Bockmuhl (1996) *Laryngor.* 75: 408-414), brain (Mohapatra (1995) *Genes Chromosomes Cancer* 13: 86-93), pancreas (Solinas-Toldo (1996) *Genes Chromosomes Cancer* 20:399-407).

A number of studies have elucidated genetic alterations that occur during the development of colorectal tumors. For instance, deletions of p53 genes on chromosome 17p are often late events associated with the transition from the benign (adenoma) to the malignant (carcinoma) state. See Vogelstein et al., *New England Journal of Medicine,* 319:525 (1988), Fearon and Vogelstein, *Cell,* 61:759-767 (1990) and Baker et al. *Cancer Res.* 50:7717-22 (1990). More recently, comparative genomic hybridization has shown that specific patterns of chromosomal gains and losses take place during colorectal carcinogenesis (see, e.g. Schlegel, et al. *Cancer Research.* 55, 6002-6005 (1995); Ried, et al. *Genes, Chromosomes & Cancer* 15, 234-245 (1996); and Nakao et al., *Jpn. J. Surg.* 28, 567-569 (1998). These changes included overrepresentation (amplification) of large portion of chromosome 20 material.

The identification of new genes that are responsible for carcinogenesis is obviously great use in diagnosis, prognosis and treatment of these diseases. The present invention addresses these and other needs.

BRIEF SUMMARY OF THE INVENTION

This invention provides a method for determining the presence or absence of a colorectal cancer cell in a patient, by determining the level of a target nucleic acid that encodes the 26#77 protein (e.g., SEQ ID NO: 2) in a biological sample from the patient. In one embodiment, the target nucleic acid comprises a sequence at least 80% identical to SEQ ID NO: 1. In a further embodiment, the biological sample can include isolated nucleic acids. In another embodiment, the nucleic acids are amplified before the level of the target nucleic acid is determined. In an additional embodiment the isolated nucleic acids are mRNA.

In one aspect, the biological sample is colorectal tissue and the step of determining the level of target nucleic acid is carried out using in situ hybridization.

In another aspect, the step of determining the level of target nucleic acid is carried out using a labeled nucleic acid probe that selectively hybridizes to SEQ ID NO: 1 under stringent hybridization conditions. The nucleic acid probe can be immobilized to a solid support. In a further aspect, the step of determining the level of target nucleic acid is carried out using Northern blot analysis.

In one embodiment, the step of determining the level of the target nucleic acid is carried out by comparing the amount of the target nucleic acid in the biological sample to the amount of the target nucleic acid in a reference sample. The reference sample can be from normal colorectal tissue.

In another embodiment, the levels of 26#77 encoding nucleic acid are determined when the patient is undergoing a therapeutic regimen to treat colorectal cancer. The levels of 26#77 encoding nucleic acid can also be determined when the patient is suspected of having colorectal cancer.

In one embodiment this invention provides an isolated expression vector with a nucleic acid sequence that encodes SEQ ID NO: 2, the 26#77 protein. In further embodiments, the nucleic acid sequence is at least 80% identical to SEQ ID NO: 1. The invention also provides a host cell containing a vector that expresses a nucleic acid that encodes the 26#77 protein.

In one embodiment this invention provides a method for determining the presence or absence of a colorectal cancer cell in a patient, by determining the level of a target protein, the 26#77 protein including the sequence shown in SEQ ID NO: 2. Levels of the 26#77 protein are determined in a biological sample from the patient, thereby determining the presence or absence of the colorectal cancer cell in the patient. In one aspect the 26#77 protein levels are determined by using an antibody specific for the 26#77 protein. The antibody can be a polyclonal antibody or a monoclonal antibody. In a further aspect, the antibody can be labeled and the label can be a fluorescent label.

In a further embodiment, the step of determination of the level of the 26#77 protein is carried out by comparing the amount of the 26#77 protein in the biological sample to the amount of the 26#77 protein in a reference sample. In one aspect, the reference sample is from normal colorectal tissue. In another aspect, the determination of 26#77 protein level is made when the patient is undergoing a therapeutic regimen to treat colorectal cancer. In a further aspect, the determination of 26#77 protein level is made when the patient is suspected of having colorectal cancer.

In one embodiment, the present invention provides a method for treating a cancer that overexpresses a 26#77 gene product by administering a therapeutically effective amount of an inhibitor of 26#77 gene product to a patient who a cancer that overexpresses 26#77. The inhibitor of the 26#77 gene product can be an antisense RNA molecule, or an inhibitory RNA molecule.

Definitions

The phrase "determining the level of a target nucleic acid" refers to any method that can be used to detect increased copy number of a genomic sequence or increased expression level of a target gene. Methods for determining increased copy number are well known and include nucleic acid hybridization methods as described below. Methods for determining the level of expression of a particular gene are well known in the art. Such methods include RT-PCR, real-time PCR, use of antibodies against the gene products, and the like. As explained below, methods of the invention are used to detect increased copy number or overexpression of a gene referred to here as 26#77. Typically, overexpression of a particular gene is at least about 2 times, usually at least about 5 times the level of expression in a normal cell from the same tissue.

The terms "26#77 protein" or "26#77polynucleotide" or refer to nucleic acid and polypeptide polymorphic variants, alleles, mutants, and interspecies homologues of SEQ ID NO: 1 or SEQ ID NO: 2. Typically such genes or proteins have a sequence that has greater than about 70% nucleotide sequence identity, usually 80%, 85%, 90% or 99% or greater sequence identity to SEQ ID NO: 1 or SEQ ID NO: 2, preferably over a region of over a region of at least about 25, 50, 100, 200, 500, 1000, or more residues. A polynucleotide or polypeptide sequence is typically from a mammal including, but not limited to, primate, e.g., human; rodent, e.g., rat, mouse, hamster; cow, pig, horse, sheep, or other mammal. These terms include both naturally occurring or recombinant forms.

A "biological sample" as used herein is a sample of biological tissue or fluid that contains nucleic acids or polypeptides, e.g., of a 26#77 protein, polynucleotide or transcript. Such samples include, but are not limited to, tissue isolated from humans, or rodents, e.g., mice, and rats. Biological samples may also include sections of tissues such as biopsy and autopsy samples, frozen sections taken for histologic purposes, blood, plasma, serum, sputum, stool, tears, mucus, hair, skin, etc. Biological samples also include explants and primary and/or transformed cell cultures derived from patient tissues. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish. Livestock and domestic animals are of particular interest.

"Providing a biological sample" means to obtain a biological sample for use in methods described in this invention. Most often, this will be done by removing a sample of cells from an animal, but can also be accomplished by using previously isolated cells (e.g., isolated by another person, at another time, and/or for another purpose), or by performing the methods of the invention in vivo. Archival tissues, having treatment or outcome history, will be particularly useful.

The terms "identical" or percent "identity," in the context of two or more nucleic acids or polypeptide sequences, refer to two or more sequences or subsequences that are the same or have a specified percentage of amino acid residues or nucleotides that are the same (e.g., greater than about 60% amino acid sequence identity, 65%, 70%, 75%, 80%, 85%, 90%, preferably 91%, 92%, 93%, 94%, 95%, 96%, 97%, 98% or 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1981) *Adv. Appl. Math.* 2:482-489, by the homology alignment algorithm of Needleman and Wunsch (1970) *J. Mol. Biol.* 48:443-453, by the search for similarity method of Pearson and Lipman (1988) *Proc. Nat'l. Acad. Sci. USA* 85:2444-2448, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel, et al. (eds. 1995 and supplements) *Current Protocols in Molecular Biology* Lippincott.

The BLAST algorithm also performs a statistical analysis of the similarity between two sequences (see, e.g., Karlin and Altschul (1993) *Proc. Nat'l Acad. Sci. USA* 90:5873-5887). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli*, or eukaryotic cells such as yeast, insect, amphibian, or mammalian cells, such as CHO, HeLa, and the like (see, e.g., the American Type Culture Collection catalog or web site).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG, and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. In certain contexts each codon in a nucleic acid (except AUG, which is ordinarily the only codon for methionine, and TGG, which is ordinarily the only codon for tryptophan) can be modified to yield a functionally identical molecule. Accordingly, a silent variation of a nucleic acid which encodes a polypeptide is implicit in a described sequence with respect to the expression product, but not necessarily with respect to actual probe sequences.

As to amino acid sequences, one of skill will recognize that individual substitutions, deletions, or additions to a nucleic acid, peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton (1984) *Proteins* Freeman).

"Nucleic acid" or "oligonucleotide" or "polynucleotide" or grammatical equivalents used herein means at least two nucleotides covalently linked together. Oligonucleotides are typically less than about 100 nucleotides in length. A nucleic acid of the present invention will generally contain phosphodiester bonds, although in some cases, nucleic acid analogs are included that may have at least one different linkage, e.g., phosphoramidate, phosphorothioate, phosphorodithioate, or O-methylphosphoroamidite linkages (see Eckstein (1992) *Oligonucleotides and Analogues: A Practical Approach* Oxford University Press); and peptide nucleic acid backbones and linkages. For example, peptide nucleic acids (PNA) which includes peptide nucleic acid analogs can be used in the invention.

The nucleic acids may be single stranded or double stranded, as specified, or contain portions of both double stranded or single stranded sequence. As will be appreciated by those in the art, the depiction of a single strand also defines the sequence of the complementary strand; thus the sequences described herein also provide the complement of the sequence. The nucleic acid may be DNA, both genomic and cDNA, RNA, or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g., the individual units of a peptide nucleic acid, each containing a base, are referred to herein as a nucleoside.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into the ovarian cancer nucleic acids, proteins and antibodies at any position. Any method known in the art for conjugating the antibody to the label may be employed, including those methods described by Hunter, et al. (1962) *Nature* 144:945-xxx; David, et al. (1974) *Biochemistry* 13:1014-1021; Pain, et al. (1981) *J. Immunol. Meth.* 40:219-230; and Nygren (1982) *J. Histochem. and Cytochem.* 30:407-412.

An "effector" or "effector moiety" or "effector component" is a molecule that is bound (or linked, or conjugated), either covalently, through a linker or a chemical bond, or non-covalently, through ionic, van der Waals, electrostatic, or hydrogen bonds, to an antibody. The "effector" can be a variety of molecules including, e.g., detection moieties including radioactive compounds, fluorescent compounds, an enzyme or substrate, tags such as epitope tags, a toxin; activatable moieties, a chemotherapeutic agent; a lipase; an antibiotic; or a radioisotope emitting "hard" e.g., beta radiation.

A "labeled nucleic acid probe or oligonucleotide" is one that is bound, either covalently, through a linker or a chemical bond, or non-covalently, through ionic, van der Waals, electrostatic, or hydrogen bonds to a label such that the presence of the probe may be detected by detecting the presence of the label bound to the probe. Alternatively, method using high affinity interactions may achieve the same results where one of a pair of binding partners binds to the other, e.g., biotin, streptavidin.

The term "probe" or a "nucleic acid probe", as used herein, is defined to be a collection of one or more nucleic acid fragments whose hybridization to a sample can be detected. The probe may be unlabeled or labeled as described below so that its binding to the target or sample can be detected. Particularly in the case of arrays, either probe or target nucleic acids may be affixed to the array. Whether the array comprises "probe" or "target" nucleic acids will be evident from the context. Similarly, depending on context, either the probe, the target, or both can be labeled. In some embodiments, the probe may be a member of an array of spotted nucleic acids. Techniques capable of producing high density arrays can also be used for this purpose (see, e.g., Fodor (1991) *Science* 767-773; Johnston (1998) *Curr. Biol.* 8: R171-R174; Schummer (1997) *Biotechniques* 23: 1087-1092; Kern (1997) *Biotechniques* 23: 120-124; U.S. Pat. No. 5,143,854). One of skill will recognize that the precise sequence of the particular probes described herein can be modified to a certain degree to produce probes that are "substantially identical" to the disclosed probes, but retain the ability to specifically bind to (i.e., hybridize specifically to) the same targets or samples as the probe from which they were derived. Such modifications are specifically covered by reference to the individual probes described herein.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, e.g., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, e.g., through the expression of a recombinant nucleic acid as depicted above.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, e.g., wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in "Overview of principles of hybridization and the strategy of nucleic acid assays" in Tijssen (1993) *Hybridization with Nucleic Probes* (*Laboratory Techniques in Biochemistry and Molecular Biology*) (vol. 24) Elsevier. Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is typically at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C is typical for low stringency amplification, although annealing temperatures may vary between about 32-48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

"Inhibitors", and "modulators" of polynucleotides of the invention are used to refer to molecules or agents that inhibit or modulate the oncogenic effects of the proteins described here. Such agents can be identified using in vitro and in vivo assays described below. Inhibitors are compounds that, e.g., bind to, partially or totally block activity, decrease, prevent, delay activation, inactivate, desensitize, or down regulate the activity or expression of the 26#77 proteins described here. Such agents include, for example, antisense or inhibitory RNAs which inhibit expression of the 26#77 gene. Assays for inhibitors include, e.g., expressing the 26#77 protein in vitro, in cells, or cell membranes, applying test compounds, and then determining the functional effects on activity (e.g., changes in growth of the cell). Changes in cell growth could be any property associated with a neoplastic phenotype, for example, cell viability, formation of foci, anchorage independence, semi-solid or soft agar growth, change in contact inhibition or density limitation of growth, loss of growth factor or serum requirements, change in cell morphology, gain or loss of immortalization, gain or loss of tumor specific markers, ability to form or suppress tumors when injected into suitable animal hosts, and/or immortalization of the cell.

"Tumor cell" refers to pre-cancerous, cancerous, and normal cells in a tumor.

"Cancer cells," "transformed" cells or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is typically associated with phenotypic changes, such as immortalization of cells, aberrant growth control, non-morphological changes, and/or malignancy.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG. See also, Pierce Catalog and Handbook, 1994-1995 (Pierce Chemical Co., Rockford, Ill.). See also, e.g., Kuby, J., *Immunology*, 3$^{rd}$ Ed., W.H. Freeman & Co., New York (1998). The term also refers to recombinant single chain Fv fragments (scFv). The term antibody also includes-bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol* :5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

An antibody immunologically reactive with a particular antigen can be generated by recombinant methods such as selection of libraries of recombinant antibodies in phage or similar vectors, see, e.g., Huse et al., *Science* 246:1275-1281 (1989); Ward et al, *Nature* 341:544-546 (1989); and Vaughan et al., *Nature Biotech.* 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The extent of the framework regions and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain of an antibody, including the heavy chain of an Fv, scFv, or Fab. References to "$V_L$" or a "VL" refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., Nature 321:522-525 (1986); Riechmann et al., Nature 332: 323-329 (1988); and Presta, Curr. Op. Struct. Biol. 2:593-596 (1992)). Humanization can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

BRIEF DESCRIPTION OF THE DRAWINGS

FIG. 1 illustrates a comparison of Northern and Western blots showing that both RNA and protein expression of 26#77 are higher in colorectal cancers with an amplified 26#77 gene (T) compared to the patients' normal colorectal tissue (N).

DETAILED DESCRIPTION

This invention provides novel therapeutic and diagnostic methods for treatment and detection of cancer, as well as methods for screening for compositions which can be used to treat cancer. As shown below, the invention is based, at least in part, on the discovery that 26#77 is overexpressed in colorectal and breast cancer cells. The overexpression of this gene therefore facilitates progression of carcinogenesis.

Methods of Screening for increased copy number or overexpression of 26#77 Genes

In one aspect, 26#77 genes (or their expression levels) are detected in different patient samples for which either diagnosis or prognosis information is desired. For example, the presence of cancer is evaluated by a determination of the increased copy number of 26#77 genes in the patient. Methods of evaluating the presence and/or copy number of a particular gene or to determine the presence or absence of polymorphisms in the gene are well known to those of skill in the art. For example, hybridization based assays can be used for these purposes.

Hybridization-Based Assays

Hybridization assays can be used to detect copy number of 26#77 function. Hybridization-based assays include, but are not limited to, traditional "direct probe" methods such as Southern blots or in situ hybridization (e.g., FISH), and "comparative probe" methods such as comparative genomic hybridization (CGH). The methods can be used in a wide variety of formats including, but not limited to substrate—(e.g. membrane or glass) bound methods or array-based approaches as described below.

In a typical in situ hybridization assay, cells or tissue sections are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. Preferred probes are sufficiently long so as to specifically hybridize with the target nucleic acid(s) under stringent conditions. The preferred size range is from about 200 bp to about 1000 bases.

In some applications it is necessary to block the hybridization capacity of repetitive sequences. Thus, in some embodiments, tRNA, human genomic DNA, or Cot-1 DNA is used to block non-specific hybridization.

In comparative genomic hybridization methods a first collection of (sample) nucleic acids (e.g. from a possible tumor) is labeled with a first label, while a second collection of (control) nucleic acids (e.g. from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number.

Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology, Vol.* 33: *In Situ Hybridization Protocols*, Choo, ed., Humana Press, Totowa, N.J. (1994), etc. In one particularly preferred embodiment, the hybridization protocol of Pinkel et al. (1998) *Nature Genetics* 20: 207-211, or of Kallioniemi (1992) *Proc. Natl Acad Sci USA* 89:5321-5325 (1992) is used.

A variety of nucleic acid hybridization formats are known to those skilled in the art. For example, common formats include sandwich assays and competition or displacement assays. Hybridization techniques are generally described in Hames and Higgins (1985) *Nucleic Acid Hybridization, A Practical Approach*, IRL Press; Gall and Pardue (1969) *Proc. Natl. Acad. Sci. USA* 63: 378-383; and John et al. (1969) *Nature* 223: 582-587.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

Typically, labeled signal nucleic acids are used to detect hybridization. The labels may be incorporated by any of a number of means well known to those of skill in the art. Means of attaching labels to nucleic acids include, for example nick translation, or end-labeling by kinasing of the nucleic acid and subsequent attachment (ligation) of a linker joining the sample nucleic acid to a label (e.g., a fluorophore). A wide variety of linkers for the attachment of labels to nucleic acids are also known. In addition, intercalating dyes and fluorescent nucleotides can also be used.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent labels (e.g., fluorescein, texas red, rhodamine, green fluorescent protein, and the like, see, e.g., Molecular Probes, Eugene, Oreg., USA), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The label may be added to the nucleic acids prior to, or after the hybridization. So called "direct labels" are detectable labels that are directly attached to or incorporated into the sample or probe nucleic acids prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol.* 24: *Hybridization With Nucleic Acid Probes*, P. Tijssen, ed. Elsevier, N.Y., (1993)).

The methods of this invention are particularly well suited to array-based hybridization formats. For a description of one preferred array-based hybridization system see Pinkel et al. (1998) *Nature Genetics,* 20: 207-211.

Arrays are a multiplicity of different "probe" or "target" nucleic acids (or other compounds) attached to one or more surfaces (e.g., solid, membrane, or gel). In a preferred embodiment, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606-614; Jackson (1996) *Nature Biotechnology* 14:1685; Chee (1995) *Science* 274: 610; WO 96/17958, Pinkel et al. (1998) *Nature Genetics* 20: 207-211).

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

The DNA used to prepare the arrays of the invention is not critical. For example the arrays can include genomic DNA, e.g. overlapping clones that provide a high resolution scan of a portion of the genome containing the desired gene, or of the gene itself. Genomic nucleic acids can be obtained from, e.g., HACs, MACs, YACs, BACs, PACs, P1s, cosmids, plasmids, inter-Alu PCR products of genomic clones, restriction digests of genomic clones, cDNA clones, amplification (e.g., PCR) products, and the like.

Arrays can also be produced using oligonucleotide synthesis technology. Thus, for example, U.S. Pat. No. 5,143,854 and PCT Patent Publication Nos. WO 90/15070 and 92/10092 teach the use of light-directed combinatorial synthesis of high density oligonucleotide arrays.

Amplification-Based Assays.

In other embodiments, amplification-based assays can be used to measure 26#77 gene copy number in a sample. In such amplification-based assays, the nucleic acid sequences act as a template in an amplification reaction (e.g. Polymerase Chain Reaction (PCR). In a quantitative amplification, the amount of amplification product will be proportional to the amount of template in the original sample. Comparison to appropriate (e.g. healthy tissue) controls provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.). The known nucleic acid sequence for the genes is sufficient to enable one of skill to routinely select primers to amplify any portion of the gene.

Real time PCR is another amplification technique that can be used to determine gene copy levels or levels of mRNA expression. (See, e.g., Gibson et al., Genome Research 6:995-1001, 1996; Heid et al., Genome Research 6:986-994, 1996). Real-time PCR is a technique that evaluates the level of PCR product accumulation during amplification. This technique permits quantitative evaluation of mRNA levels in multiple samples. For gene copy levels, total genomic DNA is isolated from a sample. For mRNA levels, mRNA is extracted from tumor and normal tissue and cDNA is prepared using standard techniques. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, β-actin) primers and probes may be obtained commercially from, for example, Perkin Elmer/Applied Biosystems (Foster City, Calif.). To quantitate the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from $10$-$10^6$ copies of the gene of interest are generally sufficient. In addition, a standard curve is generated for the control sequence. This permits standardization of initial content of the nucleic acid of interest in a tissue sample to the amount of control for comparison purposes.

Other suitable amplification methods include, but are not limited to ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.

Detection of 26#77 Gene Expression

26#77 gene expression level can also be assayed as a marker for cancer. In preferred embodiments, activity of the 26#77 gene is determined by a measure of gene transcript (e.g. mRNA), by a measure of the quantity of translated protein, or by a measure of gene product activity.

Methods of detecting and/or quantifying the gene transcript (mRNA or cDNA) using nucleic acid hybridization techniques are known to those of skill in the art (see Sambrook et al. supra). For example, one method for evaluating the presence, absence, or quantity of mRNA involves a Northern blot transfer.

The probes can be full length or less than the full length of the nucleic acid sequence encoding the protein. Shorter probes are empirically tested for specificity. Preferably nucleic acid probes are 20 bases or longer in length. (See Sambrook et al. for methods of selecting nucleic acid probe sequences for use in nucleic acid hybridization.) Visualization of the hybridized portions allows the qualitative determination of the presence or absence of mRNA.

In another preferred embodiment, a transcript (e.g., mRNA) can be measured using amplification (e.g. PCR) based methods as described above for directly assessing copy number of DNA. In a preferred embodiment, transcript level is assessed by using reverse transcription PCR (RT-PCR). In another preferred embodiment, transcript level is assessed by using real-time PCR.

The expression level of an 26#77 gene can also be detected and/or quantified by detecting or quantifying the expressed 26#77 polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like. Immunohistochemical methods can also be used to detect 26#77 protein. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al. (1980) *Am. J. Clin. Path.* 75:734-738. The isolated proteins can also be sequenced according to standard techniques to identify polymorphisms.

The 26#77 polypeptide is detected and/or quantified using any of a number of well recognized immunological binding assays (see, e.g., U.S. Pat. Nos. 4,366,241; 4,376,110; 4,517,288; and 4,837,168). For a review of the general immunoassays, see also Asai (1993) *Methods in Cell Biology Volume 37: Antibodies in Cell Biology*, Academic Press, Inc. New York; Stites & Terr (1991) *Basic and Clinical Immunology 7th Edition*.

Immunological binding assays (or immunoassays) typically utilize a "capture agent" to specifically bind to and often immobilize the analyte (polypeptide or subsequence). The capture agent is a moiety that specifically binds to the analyte. In a preferred embodiment, the capture agent is an antibody that specifically binds a polypeptide. The antibody (anti-peptide) may be produced by any of a number of means well known to those of skill in the art.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled polypeptide or a labeled anti-antibody. Alternatively, the labeling agent may be a third moiety, such as another antibody, that specifically binds to the antibody/polypeptide complex.

In one preferred embodiment, the labeling agent is a second human antibody bearing a label. Alternatively, the second antibody may lack a label, but it may, in turn, be bound by a labeled third antibody specific to antibodies of the species from which the second antibody is derived. The second can be modified with a detectable moiety, e.g., as biotin, to which a third labeled molecule can specifically bind, such as enzyme-labeled streptavidin. In some embodiments, Western blot analysis is used to detected and or quantify 26#77 protein.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401-1406, and Akerstrom (1985) *J. Immunol.*, 135: 2589-2542).

26#77 protein can be detected and/or quantified in cells using immunocytochemical or immunohistochemical methods. IHC (immunohistochemistry) can be performed on paraffin-embedded tumor blocks using a 26#77-specific antibody. IHC is the method of colormetric or fluorescent detection of archival samples, usually paraffin-embedded, using an antibody that is placed directly on slides cut from the paraffin block. To detect and/or quantify 26#77 in, for example tissue culture cells or cells from a subject that are not embedded in paraffin (for example, hematopoetic cells) ICC (immunocytochemistry) can be used. ICC is like IHC but uses fresh, non-paraffin embedded cells plated onto slides and then fixed and stained.

Either polyclonal or monoclonal antibodies may be used in the immunoassays of the invention described herein. Polyclonal antibodies are preferably raised by multiple injections (e.g. subcutaneous or intramuscular injections) of substantially pure polypeptides or antigenic polypeptides into a suitable non-human mammal. The antigenicity of peptides can be determined by conventional techniques to determine the magnitude of the antibody response of an animal that has been immunized with the peptide. Generally, the peptides that are used to raise the anti-peptide antibodies should generally be those which induce production of high titers of antibody with relatively high affinity for the polypeptide.

Preferably, the antibodies produced will be monoclonal antibodies ("mAb's"). For preparation of monoclonal antibodies, immunization of a mouse or rat is preferred. Polyclonal antibodies can also be used.

It is also possible to evaluate an mAb to determine whether it has the same specificity as a mAb of the invention without undue experimentation by determining whether the mAb being tested prevents a mAb of the invention from binding to the subject gene product isolated as described above. If the mAb being tested competes with the mAb of the invention, as shown by a decrease in binding by the mAb of the invention, then it is likely that the two monoclonal antibodies bind to the same or a closely related epitope. Still another way to determine whether a mAb has the specificity of a mAb of the invention is to preincubate the mAb of the invention with an antigen with which it is normally reactive, and determine if the mAb being tested is inhibited in its ability to bind the antigen. If the mAb being tested is inhibited then, in all likelihood, it has the same, or a closely related, epitopic specificity as the mAb of the invention.

The assays of this invention have immediate utility in detecting/predicting the likelihood of a cancer, in estimating survival from a cancer, in screening for agents that modulate the subject gene product activity, and in screening for agents that inhibit cell proliferation.

Methods of Screening for 26#77 Function

Assays for 26#77 function can be designed to detect and/or quantify any effect that is indirectly or directly under the influence of the 26#77 protein or nucleic acid, e.g., a functional, physical, or chemical effect. Such assays can be used to test whether a biological sample comprises a functional 26#77 protein, to test whether variant 26#77 polypeptides retain function, or to identify compounds that modulate 26#77 activity in cells.

Typical assays useful in the present invention are those designed to test neoplastic characteristics of cancer cells. These assays include cell growth on soft agar; anchorage dependence; contact inhibition and density limitation of growth; cellular proliferation; cell death (apoptosis); cellular transformation; growth factor or serum dependence; tumor specific marker levels; invasiveness into Matrigel; tumor growth and metastasis in vivo; mRNA and protein expression in cells undergoing metastasis, and other characteristics of cancer cells.

The ability of 26#77 polynucleotides to promote cell growth can also be assessed by introducing the polynucleotides into in cells and assessing the growth of those cells in vitro or in vivo.

Assays may include those designed to test the ability of test agents to bind the 26#77 protein and thereby modulate its activity. Virtually any agent can be tested in such an assay. Such agents include, but are not limited to antibodies, natural or synthetic nucleic acids, natural or synthetic polypeptides, natural or synthetic lipids, natural or synthetic small organic molecules, and the like.

Proteins interacting with the peptide or with the protein encoded by the cDNA (e.g., 26#77) can be isolated using a yeast two-hybrid system, mammalian two hybrid system, or phage display screen, etc. Targets so identified can be further used as bait in these assays to identify additional proteins that interact with 26#77 or are downstream of 26#77, which proteins are also targets for drug development (see, e.g., Fields et al., *Nature* 340:245 (1989); Vasavada et al., *Proc. Nat'l Acad. Sci. USA* 88:10686 (1991); Fearon et al., *Proc. Nat'l Acad. Sci. USA* 89:7958 (1992); Dang et al., *Mol. Cell. Biol.* 11:954 (1991); Chien et al., *Proc. Nat'l Acad. Sci. USA* 9578 (1991); and U.S. Pat. Nos. 5,283,173, 5,667,973, 5,468,614, 5,525, 490, and 5,637,463).

Any of the assays for detecting 26#77 binding are amenable to high throughput screening. High throughput assays for the presence, absence, or quantification of particular nucleic acids or protein products are well known to those of skill in the art. Similarly, binding assays and reporter gene assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Recombinant Production of 26#77 Polypeptides

The present invention also provides methods, reagents, and vectors useful for expression of 26#77 polypeptides and nucleic acids in vitro. In vitro expression is particularly useful for production of 26#77 polypeptides.

Any number of well known host cells can be used for production of 26#77 polypeptides. Host cells may be cultured cells, cell lines, cells in vivo, and the like. Host cells may be prokaryotic cells such as bacterial cells, (e.g., *E. coli*), or eukaryotic cells such as yeast, insect, amphibian, or mammalian cells such as CHO, HeLa, and the like.

The particular procedure used to introduce the nucleic acids into a host cell for expression of the 26#77 protein is not critical to the invention. Any of the well known procedures for introducing foreign nucleotide sequences into host cells in vitro may be used. These include the use of calcium phosphate transfection, electroporation, liposome-mediated transfection, injection and microinjection, ballistic methods, viral particles, virosomes, immunoliposomes, polycation:nucleic acid conjugates, naked DNA, artificial virions, agent-enhanced uptake of DNA, and the like.

In these embodiments of this invention, 26#77 nucleic acids are inserted into vectors using standard molecular biological techniques. Vectors may be used at multiple stages of the practice of the invention, including for subcloning nucleic acids encoding components of the 26#77 protein as well as additional elements controlling protein expression, vector selectability, etc. Vectors may also be used to maintain or amplify the nucleic acids, for example by inserting the vector into prokaryotic or eukaryotic cells and growing the cells in culture. In addition, vectors may be used to introduce and express nucleic acids into cells for therapeutic or experimental purposes.

A variety of commercially or commonly available vectors and vector nucleic acids can be converted into a vector of the invention by cloning a nucleic acid encoding a 26#77 protein of the invention into the commercially or commonly available vector. A variety of common vectors suitable for this purpose are well known in the art.

In a typical embodiment, an 26#77 poynucleotide is placed under the control of a promoter. A nucleic acid is "operably linked" to a promoter when it is placed into a functional relationship with the promoter. For instance, a promoter or enhancer is operably linked to a coding sequence if it increases or otherwise regulates the transcription of the coding sequence. Similarly, a "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include promoters and, optionally, introns, polyadenylation signals, and transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

An extremely wide variety of promoters are well known, and can be used in the vectors of the invention, depending on the particular application. Ordinarily, the promoter selected depends upon the cell in which the promoter is to be active. Other expression control sequences such as ribosome binding sites, transcription termination sites and the like are also optionally included. For E. coli, example control sequences include the T7, trp, or lambda promoters, a ribosome binding site and preferably a transcription termination signal. For eukaryotic cells, the control sequences typically include a promoter which optionally includes an enhancer derived from immunoglobulin genes, SV40, cytomegalovirus, a retrovirus (e.g., an LTR based promoter) etc., and a polyadenylation sequence, and may include splice donor and acceptor sequences.

For long-term, high-yield production of recombinant proteins, stable expression will often be desired. For example, cell lines which stably express a 26#77 protein can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type. An amplification step, e.g., by administration of methyltrexate to cells transfected with a DHFR gene according to methods well known in the art, can be included.

Kits Use in Diagnostic, Research, and Therapeutic Applications

For use in diagnostic, research, and therapeutic applications disclosed here, kits are also provided by the invention. In the diagnostic and research applications such kits may include any or all of the following: assay reagents, buffers, 26#77-specific nucleic acids or antibodies, hybridization probes and/or primers, and the like. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

The present invention also provides for kits for screening for modulators of 26#77. Such kits can be prepared from readily available materials and reagents. For example, such kits can comprise one or more of the following materials: an 26#77 polypeptide or polynucleotide, reaction tubes, and instructions for testing the desired 26#77 function.

A wide variety of kits and components can be prepared according to the present invention, depending upon the intended user of the kit and the particular needs of the user. Diagnosis would typically involve evaluation of a plurality of genes or products. The genes will be selected based on correlations with important parameters in disease which may be identified in historical or outcome data.

Therapeutic Methods

Administration of Inhibitors

As noted above, inhibitors of the invention can be used to treat cancer and other diseases associated with pathological cellular proliferation. The compounds that inhibit 26#77 activity can be administered by a variety of methods including, but not limited to parenteral (e.g., intravenous, intramuscular, intradermal, intraperitoneal, and subcutaneous routes), topical, oral, local, or transdermal administration. These methods can be used for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges.

The compositions for administration will commonly comprise an inhibitor dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

The compositions containing inhibitors can be administered for therapeutic or prophylactic treatments. In therapeutic applications, compositions are administered to a patient suffering from a disease (e.g., colon cancer) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient.

Polynucleotide Inhibitors of 26#77 Genes

The activity of 26#77 protein can also be down-regulated, or entirely inhibited, by the use of antisense polynucleotides, e.g., a nucleic acid complementary to, and which can preferably hybridize specifically to, a 26#77 encoding mRNA. Binding of the antisense polynucleotide to the mRNA reduces the translation and/or stability of the mRNA.

Antisense polynucleotides can comprise naturally-occurring nucleotides, or synthetic species formed from naturally-occurring subunits or their close homologs. Antisense polynucleotides may also have altered sugar moieties or inter-sugar linkages. Exemplary among these are the phosphorothioate and other sulfur containing species which are known for use in the art. Analogs are comprehended by this invention so long as they function effectively to hybridize with the ovarian cancer protein mRNA. See, e.g., Isis Pharmaceuticals, Carlsbad, Calif.; Sequitor, Inc., Natick, Mass.

RNA interference is another mechanism to suppress gene expression in a sequence specific manner. See, e.g., Brumelkamp, et al. (2002) *Sciencexpress* (21Mar., 2002); Sharp (1999) *Genes Dev.* 13:139-141; and Cathew (2001) *Curr. Op. Cell Biol.* 13:244-248. In mammalian cells, short, e.g., 21 nt, double stranded small interfering RNAs (siRNA) have been shown to be effective at inducing an RNAi response. See, e.g., Elbashir, et al. (2001) *Nature* 411:494-498.

Ribozymes can also be used to target and inhibit transcription of 26#77 nucleotide sequences. A ribozyme is an RNA molecule that catalytically cleaves other RNA molecules. Different kinds of ribozymes have been described, including group I ribozymes, hammerhead ribozymes, hairpin ribozymes, RNase P, and axhead ribozymes (see, e.g., Castanotto, et al. (1994) *Adv. Pharmacol.* 25: 289-317 for a general review of the properties of different ribozymes).

The polynucleotide inhibitors can be introduced into a cancer cell by any of a number of well known techniques. For example, the polynucleotide inhibitors can be conjugated to a binding molecule, as described in WO 91/04753. Suitable binding molecules include, but are not limited to, molecules that bind cell surface receptors on the surface of the target cancer cell. Preferably, conjugation of the binding molecule does not substantially interfere with the ability of the binding molecule to bind to its corresponding receptor, or block entry of the inhibitory polynucleotide into the cell. Alternatively, a polynucleotide inhibitor may be introduced into a cell containing the target nucleic acid sequence by formation of an polynucleotide-lipid complex.

EXAMPLES

The following examples are offered to illustrate, but not to limit the claimed invention.

Example 1

Unknown Gene 26#77 is Amplified and Overexpressed at the RNA and Protein Levels in Primary Human Colorectal Cancers Chromosome 20q is amplified in approximately 60% of primary human colorectal cancers. However, no definitive gene target has been identified for the amplicon in human colorectal cancers.

Unknown gene 26#77 was originally identified by virtue of its RNA expression profile in a breast cancer cell line. Recombinant 26#77 protein was expressed and used to generate antibodies specific for the 26#77protein.

Twelve breast and colorectal cancer cell lines were tested for 26#77 DNA amplification and for RNA and protein levels. The 26#77 gene was amplified in three of twelve breast and colorectal cancer cell lines tested by Southern blot analysis or FISH. Northern blot analysis demonstrated that 26#77 RNA levels were elevated in nine of the twelve breast and colorectal cancer cell lines tested.

The 26#77 protein was predominantly localized in the nucleus. A colorectal cancer cell line (CACO2 cell line) was fractionated into cytoplasmic and nuclear fractions. Western blot analysis with the ant 26#77 polyclonal antibody demonstrated that the majority of 26#77 protein was found in the nuclear fraction. Immunocytochemical analysis of CACO2 cells also showed that 26#77 was predominantly localized in the nucleus. Similar results were obtained using a breast cancer cell line (BT474) that overexpressed 26#77.

26#77 was also cloned into a tetracycline-inducible vector (from Invitrogen). The tet-inducible 26#77 vector was then used to transfect NIH 3T3 cells. After induction of 26#77 expression, 26#77 was localized to the cell nucleus as demonstrated by western blot analysis and immunocytochemistry.

One hundred and twenty-five primary colorectal cancers with the 20q amplicon were tested for 26#77 gene copy levels. The 26#77 gene was amplified in 60% of the 125 colorectal cancers tested by Southern blot analysis or FISH. A subset of the 125 primary colorectal cancers (40 samples total) were tested for 26#77 RNA and protein levels. Of the 26#77 amplified colorectal cancers in the subset (20 cancers total), all had elevated levels of 26#77 RNA compared to matched normal colorectal tissue as demonstrated by Northern blot analysis. Exemplary results are shown in FIG. 1.

Western blot analysis and immunohistochemistry demonstrated that 26#77 protein levels were also elevated in the samples. The results indicate that the 26#77 gene is a target of the 20q amplicon and is an important novel oncogene in human colorectal cancer.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for determining the presence or absence of a colorectal cancer cell in a patient, the method comprising determining the level of a target nucleic acid that comprises a sequence at least 99% identical to SEQ ID NO: 1, wherein the level of the target nucleic acid is determined in a colorectal tissue sample from the patient and compared to the amount of the target nucleic acid in a reference sample, thereby determining the presence or absence of the colorectal cancer cell in the patient.

2. A method for determining the presence or absence of a colorectal cancer cell in a patient, the method comprising determining the level of a target nucleic acid that encodes the amino acid sequence of SEQ ID NO: 2, wherein the level of the target nucleic acid is determined in a colorectal tissue sample from the patient and compared to the amount of the target nucleic acid in a reference sample, thereby determining the presence or absence of the colorectal cancer cell in the patient.

3. The method of claim 1 or claim 2, wherein the colorectal tissue sample comprises isolated nucleic acids.

4. The method of claim 3, further comprising the step of amplifying nucleic acids before the step of determining the level of the nucleic acid.

5. The method of claim 3, wherein the isolated nucleic acids are mRNA.

6. The method of claim 1 or claim 2, wherein the step of determining the level of target nucleic acid is carried out using in situ hybridization.

7. The method of claim 1 or claim 2, wherein the step of determining the level of target nucleic acid is carried out using a labeled nucleic acid probe that selectively hybridizes to SEQ ID NO: 1 under stringent hybridization conditions, wherein the stringent hybridization is carried out at 65° C. in a buffer comprising 5×SSC and 1% SDS, followed by a wash at 65° C. in a buffer comprising 0.2×SSC and 0.1% SDS; or is carried out at 42° C. in a buffer comprising 50% formamide, 5×SSC, and 1%SDS; followed by a wash at 65° C. in a buffer comprising 0.2×SSC and 0.1% SDS.

8. The method of claim 1 or claim 2, wherein the step of determining the level of target nucleic acid is carried out using a nucleic acid probe immobilized to a solid support, wherein the probe selectively hybridizes to SEQ ID NO: 1 under stringent hybridization conditions, wherein the stringent hybridization is carried out at 65° C. in a buffer comprising 5×SSC and 1% SDS, followed by a wash at 65° C. in a buffer comprising 0.2×SSC and 0.1% SDS and 1% SDS; or is carried out at 42° C. in a buffer comprising 50% formamide, 5×SSC, and 1%SDS; followed by a wash at 65° C. in a buffer comprising 0.2×SSC and 0.1% SDS.

9. The method of claim 1 or claim 2, wherein the step of determining the level of target nucleic acid is carried out using Northern blot analysis.

10. The method of claim 1 or claim 2, wherein the reference sample is from normal colorectal tissue.

11. The method of claim 1 or claim 2, wherein the patient is undergoing a therapeutic regimen to treat colorectal cancer.

12. The method of claim 1 or claim 2, wherein the patient is suspected of having colorectal cancer.

13. A method for determining the presence or absence of a colorectal cancer cell in a patient, the method comprising determining the level of a target nucleic acid that comprises the sequence of SEQ ID NO: 1, wherein the level of the target nucleic acid is determined in a colorectal tissue sample from the patient and compared to the amount of the target nucleic acid in a reference sample, thereby determining the presence or absence of the colorectal cancer cell in the patient.

14. The method of claim 3, wherein the isolated nucleic acids are DNA.

15. The method of claim 1 or claim 2, wherein the step of determining the level of target nucleic acid is carried out using a micro array platform.

* * * * *